# (12) United States Patent
Mosler et al.

(10) Patent No.: US 10,299,942 B2
(45) Date of Patent: May 28, 2019

(54) PROSTHETIC FOOT INSERT AND PROSTHETIC FOOT

(75) Inventors: Lüder Mosler, Duderstadt (DE); Carsten Mönicke, Zwickau (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 14/006,276

(22) PCT Filed: Mar. 23, 2012

(86) PCT No.: PCT/EP2012/001282
§ 371 (c)(1),
(2), (4) Date: Sep. 19, 2013

(87) PCT Pub. No.: WO2012/126633
PCT Pub. Date: Sep. 27, 2012

(65) Prior Publication Data
US 2014/0012397 A1  Jan. 9, 2014

(30) Foreign Application Priority Data
Mar. 23, 2011 (DE) .................. 10 2011 014 994

(51) Int. Cl.
*A61F 2/66* (2006.01)
*A61F 2/50* (2006.01)
*A61F 2/74* (2006.01)

(52) U.S. Cl.
CPC ........ *A61F 2/66* (2013.01); *A61F 2002/5001* (2013.01); *A61F 2002/501* (2013.01); *A61F 2002/503* (2013.01); *A61F 2002/5007* (2013.01); *A61F 2002/5009* (2013.01); *A61F 2002/5079* (2013.01); *A61F 2002/6642* (2013.01); *A61F 2002/6657* (2013.01); *A61F 2002/742* (2013.01); *A61F 2002/748* (2013.01)

(58) Field of Classification Search
CPC ...... A61F 2002/6657; A61F 2002/6664; A61F 2/66; A61F 2002/6614–2002/6692
USPC ...................................... 623/53–56
See application file for complete search history.

(56) References Cited

U.S. PATENT DOCUMENTS

| 5,116,384 A | 5/1992 | Wilson et al. |
| 6,669,737 B2 | 12/2003 | Mosler et al. |
| 7,879,110 B2 | 2/2011 | Phillips |
| 8,317,876 B2 | 11/2012 | Mosler |

(Continued)

FOREIGN PATENT DOCUMENTS

| DE | 40 37 928 A1 * | 5/1992 | ............... A61F 2/66 |
| DE | 10049714 A1 | 4/2002 | |

(Continued)

OTHER PUBLICATIONS

PCT International Search Report for International Application No. PCT/EP2012/001282, dated Jul. 6, 2012.

*Primary Examiner* — David H Willse
(74) *Attorney, Agent, or Firm* — Holland & Hart, LLP (57) ABSTRACT

A prosthetic foot insert with upper attachment member, a roof spring extending forwards from the upper attachment means, and a base spring coupled to the roof spring at least two points. A rear coupling element is provided for supporting the base spring, and a free space is formed between the coupling element, the roof spring and the base spring. The base spring, in the heel area, protrudes rearwards as a free lever beyond the rear coupling element.

24 Claims, 4 Drawing Sheets

(56) References Cited

U.S. PATENT DOCUMENTS

| | | |
|---|---|---|
| 8,540,781 B2 | 9/2013 | Nissels et al. |
| 2005/0038525 A1 | 2/2005 | Doddroe et al. |
| 2006/0015192 A1 | 1/2006 | Clausen et al. |
| 2006/0069450 A1 | 3/2006 | McCarvill et al. |
| 2009/0012630 A1* | 1/2009 | Mosler .................. A61F 2/66 623/55 |
| 2009/0306792 A1 | 12/2009 | Lecomte et al. |
| 2010/0004757 A1 | 1/2010 | Clausen et al. |
| 2010/0042228 A1 | 2/2010 | Doddroe et al. |
| 2010/0312360 A1 | 12/2010 | Caspers |
| 2012/0046760 A1 | 2/2012 | Nissels et al. |

FOREIGN PATENT DOCUMENTS

| | | | |
|---|---|---|---|
| DE | 102005062231 A1 | 7/2007 | |
| DE | 102006004132 A1 | 8/2007 | |
| DE | 102010034893 A1 | 2/2012 | |
| EP | 1322265 A2 | 7/2003 | |
| EP | 1357867 B1 | 12/2006 | |
| EP | 2420212 A1 | 2/2012 | |
| FR | 2 640 499 A1 * | 6/1990 | ............... A61F 2/66 |
| RU | 2 209 611 C1 * | 8/2003 | ............... A61F 2/66 |
| RU | 2 209 612 C1 * | 8/2003 | ............... A61F 2/66 |
| SU | 560606 * | 7/1977 | ............... A61F 2/66 |

* cited by examiner

PROSTHETIC FOOT INSERT AND PROSTHETIC FOOT

TECHNICAL FIELD

The invention relates to a prosthetic foot insert with upper attachment means, a roof spring extending forward from the upper attachment means, and a base spring which has a contour convex to the ground in the forefoot area and is coupled to the roof spring at least two points, wherein a rear coupling element is provided for supporting the base spring, and a free space is formed between the coupling element, the roof spring and the base spring. The invention likewise relates to a prosthetic foot with a prosthetic foot insert and with a prosthetic foot cover.

BACKGROUND

EP 1 322 265 B1 describes a foot insert for an artificial foot, with an upper, approximately roof-shaped spring having, in the roof top area, an adapter attachment and, starting from the latter, a heel spring which extends downward in a concave curve into the heel area, and a forefoot spring which extends downward in a concave curve into the forefoot area. A base spring is connected to the free branch ends of the heel spring and of the forefoot spring, such that a spring deflection space is formed. In terms of dimensional elasticity and flexural elasticity, the base spring and the forefoot spring are configured in such a way that, under the effect of an increasing load in the forefoot area, the forefoot spring and the base spring successively bear against each other in this area. A prosthetic foot insert of this kind has good service properties, but it places high demands on the material to be used.

EP 1 357 867 B1 describes a below-knee prosthesis with an upper foot plate, and a forefoot plate and heel plate arranged below the latter and connected to the upper foot plate via an intermediate elastomeric layer, wherein the intermediate elastomeric layer holds the forefoot plate and the heel plate at a distance from each other. The gap between the forefoot plate and the heel plate is located in a middle foot portion and ensures that the plates are able to move independently of each other.

Moreover, a prosthetic foot insert with a continuous upper spring and a divided lower spring is known from the company Otto Bock. The front area of the lower spring and the rear area of the lower spring are separate from each other and are secured on the upper spring via a continuous elastomeric element. The heel compliance is produced by the elastomeric join, the forefoot compliance from the cooperation between the upper spring, the lower springs and the elastomeric element.

A further model of a prosthetic foot insert from the company Otto Bock has a continuous upper spring and a continuous lower spring, which have a continuous elastomeric join. The heel compliance is produced by the rear part of the lower spring and by the elastomeric element, the compliance in the forefoot area from the upper and lower springs and the elastomeric element. A prosthetic foot insert of this kind has a low structural height but, for this reason, also a stiff forefoot. The heel function is relatively soft and, as a result of a short free spring length, has a considerable progression.

In passive prosthetic feet, a compromise is made between standing properties and walking properties, since they lack the possibility of a muscular compensation. For improved stability when standing, feet are therefore produced with a rigid forefoot lever, whereas feet for better walking properties have softer forefoot levers. On the basis of measured values, active prosthetic feet are able to decide which activity is ongoing and can accordingly modify the properties and adjust themselves to the particular activity.

SUMMARY

The object of the present invention is to make available a prosthetic foot insert and a prosthetic foot that has good standing and walking properties and that also achieves a good load-bearing capacity with less loadable materials.

According to the invention, this object is achieved by a prosthetic foot insert having the features of the main claim. Advantageous embodiments and developments of the invention are disclosed in the dependent claims, the figures and the description.

In the prosthetic foot insert according to the invention with upper attachment means, a roof spring extending forward from the upper attachment means, and a base spring which is preferably rigid under tension and is coupled to the roof spring at least two points, wherein a rear coupling element is provided for supporting the base spring, and a free space is formed between the coupling element, the roof spring and the base spring, provision is made that the base spring, in the heel area, protrudes rearward as a free lever beyond the rear coupling element. As a result of the protrusion of the base spring, which is preferably rigid under tension and designed as a continuous leaf spring, rearward beyond the rear coupling element, a free lever is obtained which, when the heel is loaded, allows a three-point bending of the base spring, and therefore the elastic properties of the latter are better utilized. The rear coupling element, which supports the base spring on the roof spring or on the upper attachment means, serves as a hinge point or hinge mechanism about which the base spring can swing. By virtue of the generally continuous design of the rear coupling element as a strut or the like, elastic bending inside the coupling element is provided. For easier bending, a thin design of the coupling element is advantageous, or a kind of film hinge formed by a deliberately introduced weakening in the coupling element.

The base spring can have a contour that is convex to the ground, that is to say curved downward, in the forefoot area in order to influence the rollover behavior. Alternatively, a prosthesis cover can be used which has a contour worked into it and which, together with the base spring, provides the convex contour.

In one development of the invention, provision is made that the downwardly bulging forefoot area of the base spring is adjoined by an upwardly bulging mid-foot area, such that an undulating lower contour of the base spring is obtained. Seen from the front to the rear in a side view, the contour first of all slopes downward to a low point or a low area in the forefoot area, then slopes upward into the mid-foot area and thereafter slopes back down again into the heel area, wherein the end of the base spring in the heel area can have an upwardly sloping end-piece.

The rear coupling element can be designed as a bulging heel spring or as an elastomeric element.

The roof spring can be shorter than the base spring, as a result of which a particularly compact structure of the prosthetic foot insert can be obtained.

In one development of the invention, provision is made that a front coupling element is arranged at a front area of the roof spring, and the base spring protrudes forward beyond the front coupling element. It is thus possible that, when the forefoot is loaded, the spring force and bending of the base spring does not have to be effected only by the part of the base spring arranged ahead of the front coupling element, but instead a bending of the part of the base spring lying behind the front coupling element away from the roof spring takes place, such that the whole base spring takes part in the spring action. On account of the bending of the base spring in the mid-foot area away from the roof spring, a further bending or pivoting takes place about the rear coupling element or about a pivot axis formed by the rear coupling element. It is thus possible for the rear coupling element also to take part in taking up bending forces when the forefoot is loaded.

The rear coupling element can form a pivot axis for the free lever, which pivot axis extends substantially perpendicularly with respect to the direction of walking and parallel to the base spring. Thus, at a heel strike, the free lever protruding rearward beyond the coupling element is first of all deformed about the pivot axis inside the rear coupling element. Since the base spring is secured to the roof spring, and since the second coupling point of the base spring on the roof spring is thereby at a distance from the rear coupling element, the middle portion of the base spring bends away from the roof spring, such that the part of the base spring arranged between the coupling elements also takes part in the spring work at a heel strike. In this way, less loadable materials can be used, since the load is distributed over a greater spring length.

The base spring can be mounted on the roof spring, or on the upper attachment means, so as to be pivotable about a torsion axis parallel to the longitudinal extent of the base spring. This torsion axis can be provided by the coupling elements or one coupling element, such that a shifting of the base spring relative to the roof spring is possible about the torsion axis. In this way, unevenness of the ground surface can be compensated when the foot is set down, and a desired compliance can be achieved which has proven advantageous when the foot is set down slightly obliquely during walking.

The rear coupling element can terminate with the rear end of the roof spring. At least it does not protrude rearward beyond the roof spring, such that a compact structure of the prosthetic foot insert are provided by a relatively short roof spring and by coupling elements terminating substantially flush with the roof spring. The free lever of the base spring then arises from the rearward protrusion of the base spring beyond the rear coupling element.

The roof spring, the base spring and the coupling element can be formed in one piece. In particular, they can be produced from an injection-molded polymer which permits inexpensive manufacture, such that a double spring arch is formed by the roof spring and the base spring.

A front coupling element can be designed as an elastomeric element and can be arranged between the front end area of the base spring and the upwardly sloping part of the base spring.

The structure of the base spring and of the roof spring with the coupling elements is chosen such that, when the forefoot is loaded, the free space formed by these components is made smaller, by means of the roof spring and the base spring moving toward each other.

In one development of the invention, provision is made that a vacuum pump is arranged between the base spring and the roof spring. The arrangement of the vacuum pump between the base spring and the roof spring makes it possible to free the vacuum pump of structural loads, since these are taken up by the other components of the prosthetic foot insert. The relative movement between the base spring and the roof spring makes it possible to obtain a pump stroke which is sufficient to generate a vacuum, for example in order to suck air out of a prosthesis socket and thus secure the prosthesis socket firmly on a liner.

The vacuum pump can be designed as a coupling element or can be part of a coupling element. The coupling element in question is in particular the rear coupling element if it is designed as an elastomeric element or a spring element since, at a heel strike, relatively high deformation energies are taken up that can lead to a correspondingly high pump stroke. With its elastic restoring force, the coupling element itself forms the necessary counterforce for obtaining a restoring movement to the starting position. By a suitable design of the coupling element, it is possible also to establish a stroke limit in both directions, i.e. both during the compression and also during the elongation of the coupling element. The coupling element therefore also takes up tensile forces and thus serves as a stroke limiter in the context of the restoring movement. It is likewise possible, and provision is made, that the front coupling element is part of the vacuum pump or is designed as such, even though a lower impulse height is to be expected in the forefoot area than in the heel area during a gait cycle.

The invention also relates to a prosthetic foot with a prosthetic foot insert as has been described above, and with a prosthetic foot cover having a sole area with different material thicknesses. If the sole area of the prosthetic foot cover is thicker in the forefoot area and/or heel area than it is in the mid-foot area, an additional spring effect and an advantageous rollover contour are obtained.

BRIEF DESCRIPTION OF THE DRAWINGS

Illustrative embodiments of the invention are explained in more detail below with reference to the accompanying figures, in which.

DETAILED DESCRIPTION

Figure 1:
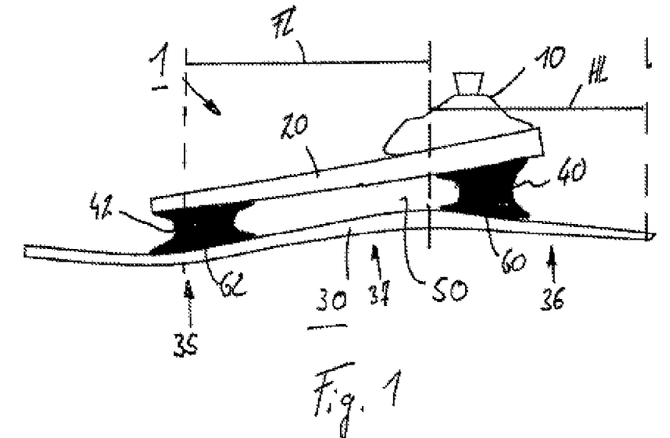
FIG. 1 shows a schematic side view of a prosthetic foot insert.

In FIG. 1, a prosthetic foot insert 1 with upper attachment means 10 in the form of an adapter pylon is shown in a schematic side view. By way of the upper attachment means 10, it is possible to attach the prosthetic foot insert 1 to a below-knee tube of a prosthetic appliance. The prosthetic foot insert 1 has a roof spring 20, which extends obliquely forward from the upper attachment means 10. The upper attachment means 10 is secured on the roof spring 20. Arranged at the rear end of the roof spring 20 there is a coupling element 40, which has a biconcave shape, i.e. has two inward curvatures. Arranged on the roof spring 20 and the rear coupling element 40 there is a base spring 30, which is designed to be rigid under tension and is in the form of a leaf spring construction in the embodiment shown. The base spring 30 is continuous and extends without interruption along the entire length, such that a closed free space 50 is formed between the roof spring 20, the rear coupling element 40 and the base spring 30.

In the illustrative embodiment shown, the base spring 30 has a forefoot area 35, which is adjoined by a mid-foot area 37, the latter ending approximately below the upper attachment means 10. The mid-foot area 37 is adjoined by a heel area 36. The lower contour of the base spring 30 has an undulating shape and, starting from the front end, firstly has a convex curvature toward the ground, i.e. a curvature with a downward bulge. The bulge can be made either continuous or sectional, wherein a continuously curved surface or contour has the advantage of a smooth rollover movement. A flattening, for example in the area of the forefoot 35, improves the stability when standing. After the contact point or contact line of the base spring 30 with the ground, the curvature continues such that the contour of the underside of the base spring 30 moves away from the ground and a free space is formed which is situated approximately in the area of the plantar arch of a natural foot and corresponds thereto. In the mid-foot area 37, a concave contour is formed which bulges in the direction of the roof spring 20 and which merges into the heel area 36. The heel area 36 can be flattened or can have a convex curvature in order to easily take up the heel strike by rolling when the prosthetic foot insert is set down. The rear end of the base spring 30 can have a convex curvature. The profile of the curvature from front to rear therefore firstly has a convex shape, then a concave shape, and then once again a convex shape.

The roof spring 20 ends approximately at the middle of the forefoot area 35 and forms a more or less straight connection of the upper spring arch 20 to the upper attachment means 10. The roof spring 20 thus acts as a strut that leads directly to the upper attachment means of the prosthetic foot insert 1, such that the forces acting on the forefoot area 35 during standing and walking are transferred to the upper attachment means 10. It will also be seen from FIG. 1 that, in the heel area 36, the base spring 30 protrudes beyond the point of connection to the rear coupling element 40. The rear coupling element 40 serves to support the base spring 30 and the so-called heel lever HL, which extends rearward from the position of the natural ankle joint, while the forefoot lever FL extends forward from the imaginary perpendicular through the position of the ankle joint. By virtue of the heel area 36 protruding beyond the point of connection of the rear coupling element 40 to the base spring 30, it is possible that, when the heel is loaded, a three-point bending of the base spring 30 occurs, such that the elastic properties of the base spring 30 are better utilized. The rear coupling element 40 thus serves as a rotation point or rotation axis 60 for the base spring 30 and effects an elastic restoring force when a bending of the base spring is effected on the rear coupling element 40 during a heel strike. The rear coupling element 40 thus serves as a hinge point or hinge site for the base spring 30 and contributes to the spring behavior, as a result of which it is possible that materials with a relatively low specific load-bearing capacity can also be used for the springs or coupling elements, and therefore the prosthetic foot insert as a whole can be produced at lower cost.

In the embodiment according to FIG. 1, the roof spring 20 and the base spring 30 are shown as separate leaf springs. The upper attachment means 10 is secured on the upper roof spring 20. The roof spring 20 and the base spring 30 are coupled to each other via two separate elastomeric elements 40, 42, for example of polyurethane. The front elastomeric element 42 and the rear elastomeric element 40 each serve as coupling elements 40, 42, such that a free space 50 is formed between the two coupling elements 40, 42 and the two springs 20, 30, said free space 50 being arranged approximately in the mid-foot area 37 of the base spring 30.

The base spring 30 is designed with a lower contour which has a convex shape in the forefoot area 35, a concave shape in the mid-foot area 37 and, in the present illustrative embodiment, a rectilinear shape in the heel area 36. Instead of the illustrated rectilinear embodiment of the base spring 30 in the heel area 36, it can also have a convex shape.

The front coupling element 42 is secured on the base spring 30 approximately in the area of the ball of the foot, and the front end of the roof spring 20, which is shorter than the base spring 30, also ends approximately at the level of the ball area 35 of the base spring 30, i.e. in the area which, when the prosthetic foot insert 1 is unloaded, rests on the ground and supports the forefoot area 35. By mounting the base spring 30 on two separate coupling elements 40, 42 which are designed as elastomeric elements, it is possible, during loading of the heel and also during loading of the forefoot, to obtain a three-point bending of the base spring 30, which also has additional cushioning and damping via the elastic coupling elements 40, 42. By virtue of the special design with a protruding spring arm in the heel area 36, it is possible to better utilize the elastic properties of the base spring 30.

The arrangement of the front coupling element 42 in the area of the ball of the foot, in the convex curvature of the base spring 30, results in a high degree of structural strength and stability of the prosthetic foot insert 1 when, after the heel strike, the forefoot touches the ground, since the roof spring 20 becomes active together with the set-down of the ball area 35. As a result of the relatively direct use of the roof spring 20 after complete set-down of the prosthetic foot, there is an abrupt increase in the effective overall spring resistance and therefore in the controllability of the prosthetic foot during contact of the ball area 35 with the ground. During the further heel-to-toe movement, the toe area of the base spring 30 is more strongly loaded, particularly toward the end of the forward roll phase, before the so-called "toe off", the main spring action being applied by the base spring 30. Since the roof spring 20 contributes only a small part of the spring action, a relatively soft heel-to-toe movement is possible. The characteristics of the heel-to-toe movement can thus be modified depending on the positioning of the front coupling element: an arrangement in the ball area 35 results in a stable set-down and soft heel-to-toe characteristics, while an arrangement further in the direction of the front end of the base spring 30 results in a soft set-down and harder push-off characteristics.

Figure 2:
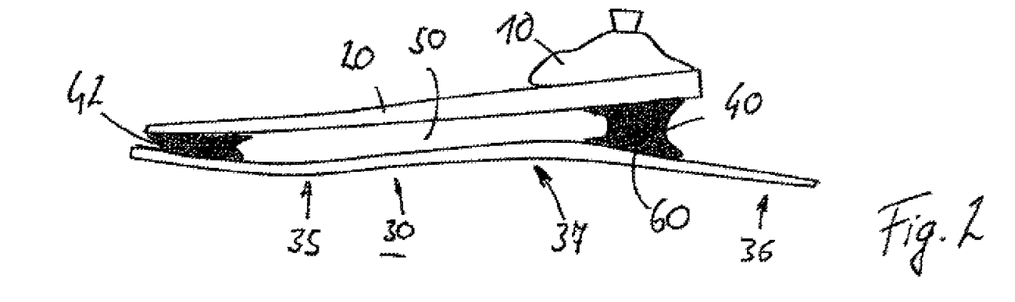
FIG. 2 shows a variant of FIG. 1.

A variant of FIG. 1 is shown in FIG. 2 and has substantially the same structure, except that the roof spring 20 extends as far as the front end of the base spring 30. The coupling of the roof spring 20 to the base spring 30 is provided via the front coupling element 42 in the toe area of the base spring, which, when the forefoot is loaded, results in the ball serving as a third bearing point for a three-point bending of the base spring 20. A prosthetic foot insert of this kind provides better control in the end phase of the stance phase. The design of the coupling elements 40, 42 as elastomeric elements permits a pivoting or tilting about an axis parallel to the longitudinal axis of the prosthetic foot insert. Bending about a pivot axis or rotation axis 60 in the area of the rear coupling element is also possible. FIG. 1 also shows a second pivot axis 62 in the front coupling element 42, such that, when the heel is loaded, a bending of the whole base spring 30 can take place at the contact point with the ground and the two axes 60, 62, such that the entire base spring 30 can be utilized for cushioning. The same also applies when the forefoot is loaded. In the variant according to FIG. 2, the front pivot axis lies in the front coupling element 42.

Figure 3:
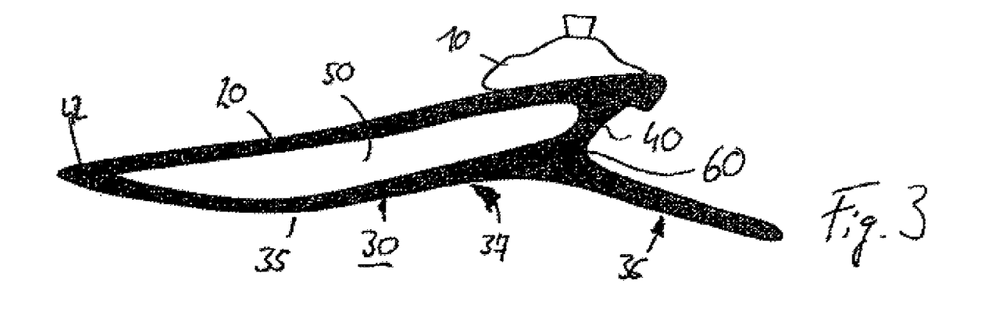
FIG. 3 shows another embodiment of a prosthetic foot insert.

FIG. 3 shows a further variant of the invention. In this case, a one-piece design of the roof spring 20 and base spring 30 together with the rear coupling element 40 is chosen. Here too, the base spring 30 in the heel area 36 protrudes rearward beyond the point of connection of the rear coupling element 40. The coupling of the roof spring 20 to the base spring 30 is provided in the toe area by fusion, such that the area where the two springs join together serves as a coupling element 42. Here too, the roof spring 20, the rear coupling element 40 and the base spring 30 are designed so as to enclose a free space 50, which can be accessible from the side. As in FIGS. 2 and 3, the lower contour of the base spring 30 has a convex forefoot shape and a concave shape in the mid-foot area 37, and the heel area 36 of the base spring 30 can have a rectilinear or convex shape. In the illustrative embodiment shown, the prosthetic foot insert 1 is designed in one piece, except for the upper attachment means 10, and is produced in particular in an injection molding method using a suitable polymer material. The rear pivot axis 60 lies in the rear coupling element 40, designed as a web. The front pivot axis (not shown) lies at the site of the connection of the roof spring 20 to the base spring 30. The hinge function of the rear coupling element 40 can be supported by specific shaping, for example a material weakness in the area in which the rotation axis is intended to lie, such that the base spring 30 can pivot about the rear coupling element 40 during bending. A corresponding design of the front coupling element 42 makes pivoting easier when the forefoot is loaded.

The arrangement of the front coupling element 42 in front of the ball area 35 as in FIG. 2, or at the front tip of the prosthetic foot insert as in FIG. 3, permits a soft set-down of the foot, since the base spring 30 with the convex curvature toward the ground can move and bend upward such that it is basically the base spring 30 alone that takes up and transfers the forces. It is only when the toe area is loaded, in general shortly before the so-called "toe off", that the roof spring 20 is perceptibly activated, which leads to an increase in the overall spring resistance at the end of the roll-over phase. With this variant, the resistance can be expressed more forcibly than if the roof spring 20 were not included.

By joining the base spring 30 via the rear coupling element 40 in the form of a web and the front coupling element 42 in the form of the connection of the base spring 30 to the roof spring 20, the rearwardly protruding heel area 36 of the base spring 30 permits, in addition to the bending that occurs inside the heel area 36, a deflection of the base spring 30, as a result of which the spring properties of the materials can be better utilized.

Figure 4:
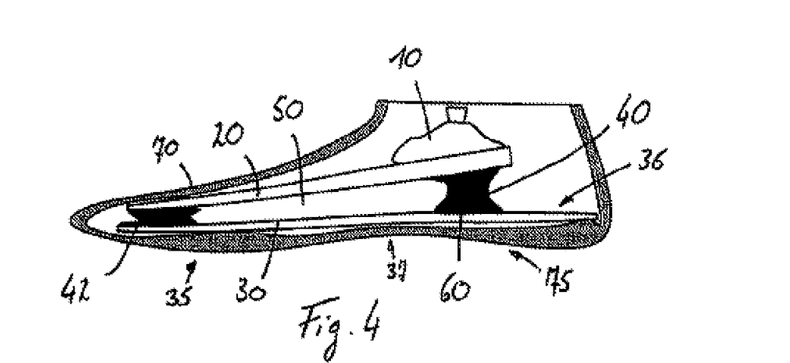
FIG. 4 shows a side view of a prosthetic foot.

FIG. 4 shows a side view of a variant of a prosthetic foot with a prosthetic foot insert according to FIG. 2. Instead of a base spring 30 with a curved contour, as is shown in FIG. 2, FIG. 4 shows a variant with a substantially straight base spring 30. Here too, the base spring 30 is connected to the roof spring 20 via elastic coupling elements 40, 42 so as to enclose a free space 50. Instead of the convex contour of the base spring 30 in the forefoot area 35, a contoured prosthesis cover 70 is provided which, in the forefoot area 35, has a thickened part which, together with the base spring 30, provides a contoured rollover contour that is convex toward the ground. The prosthesis cover 70 is made of an elastic material, for example plastic, silicone or rubber, and also has a thickened part in the heel area 36, such that, together with the base spring 30 which is likewise straight in the heel area and is designed substantially with a constant thickness, a convex overall contour curving toward the ground is also obtained here from the sole area 75 of the prosthesis cover 70 and from the base spring 30.

Figure 5:
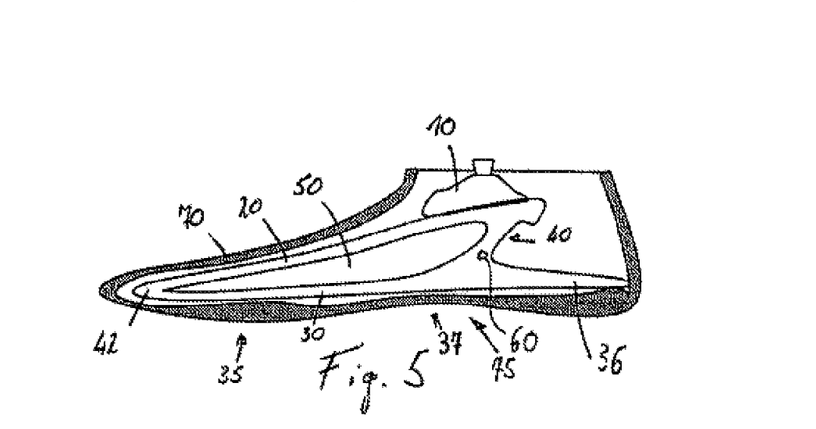
FIG. 5 shows a variant of FIG. 4.

Corresponding to the embodiment in FIG. 4, a further variant of the invention is shown in FIG. 5, where the base spring 30 and the roof spring 20 are formed in one piece. In FIG. 5 also, the base spring 30 has a substantially rectilinear design, such that a plane underside is formed. The convex contour in the forefoot area 35 and in the heel area 36 is provided by the cooperation of the rectilinear base spring 30 with the thickened areas in the sole area 75 of the prosthesis cover 70, wherein the sole area 75 has a greater material thickness in the forefoot area 35 and in the heel area 36 than in the mid-foot area 37. The increased material thickness can also be provided by separate elements which are arranged on the base spring 30 or on the prosthetic foot cover 70.

Figure 6:
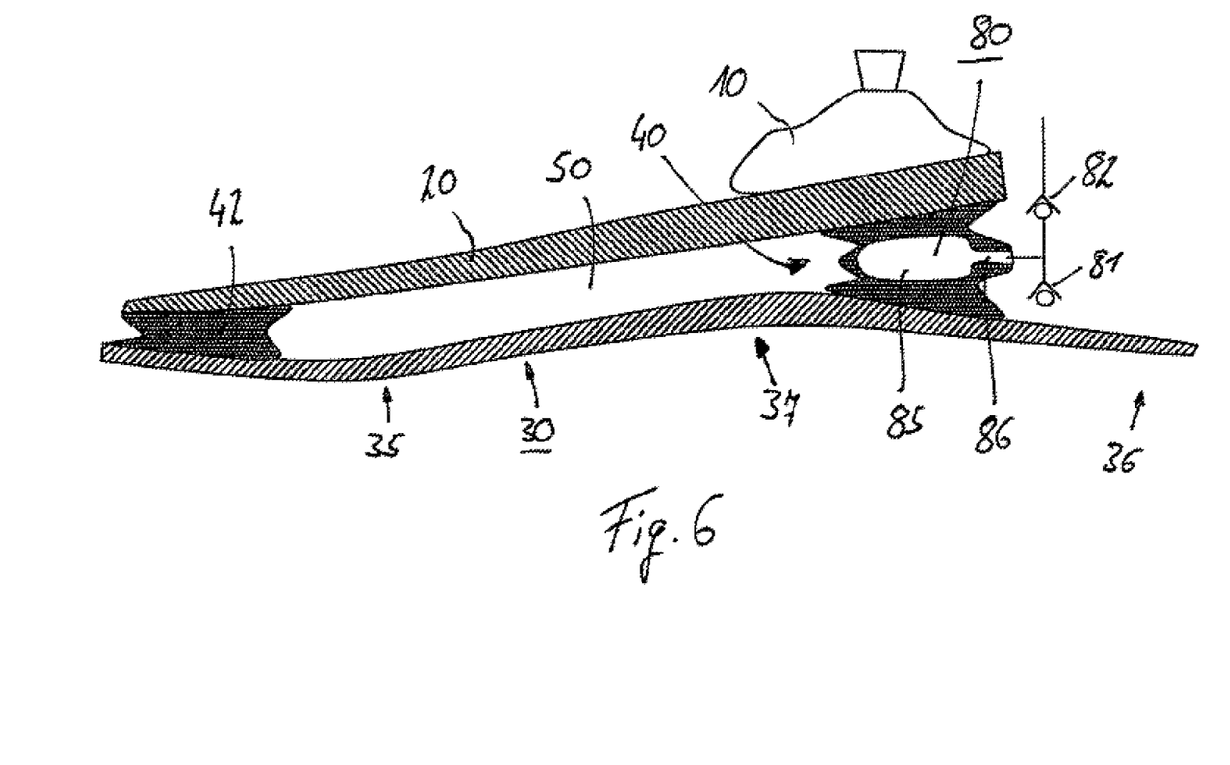
FIG. 6 shows a prosthetic foot insert with a vacuum pump.

FIG. 6 shows a variant of the invention with a vacuum pump 80. The structure of the prosthetic foot insert corresponds to that of FIG. 3, except that a vacuum pump 80 is arranged in the rear coupling element 40. The rear coupling element 40 is designed as an elastomeric element and has an elastic chamber 85, which is connected to the environment via a connecting channel 86. The connecting channel 86 is in flow connection with two nonreturn valves 81, 82. The lower nonreturn valve 81 shown in the drawing provides a block against admission of air from the environment, and the upper nonreturn valve 82 provides a block against admission of air into the area of the prosthesis to be evacuated, for example a prosthesis socket designed as a vacuum socket from which air is pumped from a space between the socket and a liner. When the rear elastomeric element 40 is compressed, the volume of the elastic chamber 85 decreases, such that the air located therein is ejected into the environment through the connecting channel 86 and the lower nonreturn valve 81. When the heel area 36 is unloaded, the rear coupling element 40 relaxes, and the roof spring 20 and the base spring 30 move away from each other at least in the heel area 36, such that the volume of the elastic chamber 85 increases again. Since no air from the environment can flow into the chamber 85 on account of the block provided by the nonreturn valve 81, air is sucked from the proximally arranged prosthesis appliance, in particular the prosthesis socket, through the non-return valve 82 and the line attached thereto.

Instead of the vacuum pump 80 being integrated in the rear coupling element 40, the vacuum pump can also be designed as a separate pump and can be arranged between the base spring 30 and the roof spring 20. The mode of operation corresponds to the above-described mode of operation, namely that a movement of the two springs 20, 30 toward each other results in a change of volume inside the chamber volume which, in the event of reduction in volume, leads to an ejection into the environment and, in the event of an increase in volume, leads to air being sucked out of the area that is to be evacuated. When the foot is unloaded and the distance of the two springs 20, 30 from each other increases, this results in the reverse movement and change of volume of the pump chamber with a correspondingly different pump direction. If a diverter mechanism is provided, it is also possible for a movement of the springs toward each other to result in an increase in volume and a suctioning of air, and for a movement of the springs away from each other to result in an ejection of air from the chamber 85.

Integration of the vacuum pump 80 in the prosthetic foot insert makes it possible to free the vacuum pump from structural loads. The pump lift can be integrated as a useful movement into the foot function, such that the structural outlay and also the mechanical outlay are greatly reduced and the overall height of the prosthetic foot can be greatly reduced. Moreover, by integrating the vacuum pump 30 in one of the coupling elements 40, 42, a function can be transferred to the pump. For example, tensile forces can be taken up by the vacuum pump 80. In addition, the stiffness of the foot and the compression rate can be influenced by controlling the valves 81, 82.

The invention claimed is:

1. A prosthetic foot insert, comprising:
   an upper attachment member;
   a roof spring extending forward from the upper attachment member and a front end with an anterior-most edge;
   a base spring;
   a front coupling element extending between the base spring and the roof spring at the anterior-most edge of the roof spring;
   a rear coupling element provided for supporting the base spring at a location spaced posterior of the front coupling element, the rear coupling element being arranged substantially in vertical alignment with the upper attachment member;
   a free space formed between the front coupling element, the rear coupling element, the roof spring, and the base spring;
   wherein a heel area of the base spring protrudes rearward as a free lever beyond a rear edge of the rear coupling element, and a ratio of a length of the base spring forward of the rear edge of the rear coupling element to a length of the free lever is in the range of about 4:1 to about 4.6:1;
   wherein the base spring bends about an axis extending parallel to the base spring and perpendicular to a walking direction during a heel strike event to provide three point bending to move a middle portion along a length of the base spring away from the roof spring in the area of the free space during the heel strike event.

2. The prosthetic foot insert as claimed in claim 1, wherein the base spring has a contour that is convex to the ground in a forefoot area.

3. The prosthetic foot insert as claimed in claim 1, wherein the base spring and the roof spring are designed as a double spring arch, and the roof spring extends as the upper arch as far as the heel area of the base spring.

4. The prosthetic foot insert as claimed in claim 1, wherein a downwardly bulging forefoot area of the base spring is adjoined by an upwardly bulging mid-foot area.

5. The prosthetic foot insert as claimed in claim 1, wherein the free space present between the roof spring and the base spring decreases in size when a forefoot is loaded.

6. The prosthetic foot insert as claimed in claim 1, wherein the rear coupling element is designed as a bulging heel spring or as an elastomeric element.

7. The prosthetic foot insert as claimed in claim 1, wherein the roof spring, the base spring and the rear coupling element are formed in one piece.

8. The prosthetic foot insert as claimed in claim 1, wherein the front coupling element is designed as an elastomeric element and arranged between a front end of the base spring and an upwardly sloping part of the base spring.

9. The prosthetic foot insert as claimed in claim 1, further comprising a vacuum pump arranged between the base spring and the roof spring.

10. The prosthetic foot insert as claimed in claim 9, wherein the vacuum pump is designed as a coupling element or is part of a coupling element.

11. A prosthetic foot with the prosthetic foot insert as claimed in claim 1 and with a prosthetic foot cover having a sole area with different material thicknesses.

12. The prosthetic foot as claimed in claim 11, wherein the sole area of the prosthetic foot cover is thicker in at least one of a forefoot area and a heel area than it is in a mid-foot area.

13. The prosthetic foot insert as claimed in claim 1, wherein the upper attachment member is configured to connect the prosthetic foot insert to a lower limb prosthetic device, and the roof spring is monolithic.

14. The prosthetic foot insert as claimed in claim 1, wherein the upper attachment member in its entirety is positioned vertically above a top surface of the roof spring, and the roof spring is monolithic.

15. A prosthetic foot insert, comprising:
   an upper attachment member;
   a roof spring connected to the upper attachment member and having a front end with an anterior-most edge;
   a base spring;
   a front coupling element extending between the base spring and the roof spring at the anterior-most edge of the roof spring;
   a rear coupling element extending between the base spring and the roof spring at a location spaced posterior of the front coupling element, the rear coupling element substantially vertically aligned with the upper attachment member;
   a free space formed between the front coupling element, the rear coupling element, the roof spring, and the base spring;
   wherein a heel area of the base spring protrudes rearward as a free lever beyond a rear edge of the rear coupling element, and a ratio of a length of the base spring forward of the rear edge of the rear coupling element to a length of the free lever is in the range of about 4:1 to about 4.6:1;
   wherein the base spring bends about an axis extending parallel to the base spring and perpendicular to a walking direction during a heel strike event to provide three point bending to move a middle portion along a length of the base spring away from the roof spring in the area of the free space during the heel strike event.

16. The prosthetic foot insert as claimed in claim 15, wherein the base spring has a contour that is convex to the ground in a forefoot area.

17. The prosthetic foot insert as claimed in claim 15, wherein the base spring and the roof spring are designed as a double spring arch, and the roof spring extends as the upper arch as far as the heel area of the base spring.

18. The prosthetic foot insert as claimed in claim 15, wherein a downwardly bulging forefoot area of the base spring is adjoined by an upwardly bulging mid-foot area.

19. The prosthetic foot insert as claimed in claim 15, wherein the free space present between the roof spring and the base spring decreases in size when a forefoot is loaded.

20. The prosthetic foot insert as claimed in claim 15, wherein the rear coupling element is designed as a bulging heel spring or as an elastomeric element.

21. The prosthetic foot insert as claimed in claim 15, wherein the roof spring, the rear base spring and the coupling element are formed in one piece.

22. The prosthetic foot insert as claimed in claim 15, wherein the front coupling element is designed as an elastomeric element and arranged between a front end of the base spring and an upwardly sloping part of the base spring.

23. A prosthetic foot insert, comprising:
an upper attachment member;
a roof spring extending forward from the upper attachment member and having a front end with an anterior-most edge;
a base spring;
a front coupling element extending between the base spring and the roof spring at the anterior-most edge of the roof spring;
a rear coupling element provided for supporting the base spring at a location spaced posterior of the front coupling element, the rear coupling element being substantially positioned in vertical alignment with the upper attachment member;
a free space formed between the front coupling element, the rear coupling element, the roof spring, and the base spring;
wherein a heel area of the base spring protrudes rearward as a free lever beyond a rear edge of the rear coupling element, and a ratio of a length of the base spring forward of the rear edge of the rear coupling element to a length of the free lever is in the range of about 4:1 to about 4.6:1;
wherein the base spring bends about an axis extending parallel to the base spring and perpendicular to a walking direction during a heel strike event to provide three point bending to move a middle portion along a length of the base spring away from the roof spring in the area of the free space during the heel strike event; and
wherein the free space present between the roof spring and the base spring decreases in size when a forefoot is loaded.

24. A prosthetic foot insert, comprising:
an upper attachment member;
a roof spring extending forward from the upper attachment member and having a front end with an anterior-most edge;
a base spring;
a front coupling element extending between the base spring and the roof spring at the anterior-most edge of the roof spring, wherein the front coupling element is designed as an elastomeric element and arranged between a front end of the base spring and an upwardly sloping part of the base spring;
a rear elastomeric coupling element provided for supporting the base spring at a location spaced posterior of the front coupling element, the location being substantially vertically aligned with the upper attachment member;
a free space formed between the front coupling element, the rear coupling element, the roof spring, and the base spring;
wherein a heel area of the base spring protrudes rearward as a free lever beyond a rear edge of the rear coupling element, and a ratio of a length of the base spring forward of the rear edge of the rear coupling element to a length of the free lever is in the range of about 4:1 to about 4.6:1;
wherein the base spring bends about an axis extending parallel to the base spring and perpendicular to a walking direction during a heel strike event to provide three point bending to move a middle portion along a length of the base spring away from the roof spring in the area of the free space during the heel strike event.

* * * * *